(12) United States Patent
Wieland et al.

(10) Patent No.: US 9,265,541 B2
(45) Date of Patent: Feb. 23, 2016

(54) INTRAMEDULLARY NAIL LOCKING HOLE ARRANGEMENT

(75) Inventors: Manfred Wieland, Kiel (DE); Stephan Petersen, Kiel (DE); Nils Zander, Eckernförde (DE)

(73) Assignee: Stryker Trauma GmbH (DE)

( * ) Notice: Subject to any disclaimer, the term of this patent is extended or adjusted under 35 U.S.C. 154(b) by 399 days.

(21) Appl. No.: 13/283,700

(22) Filed: Oct. 28, 2011

(65) Prior Publication Data

US 2013/0110111 A1     May 2, 2013

(51) Int. Cl.
*A61B 17/72* (2006.01)

(52) U.S. Cl.
CPC ............ *A61B 17/72* (2013.01); *A61B 17/7233* (2013.01)

(58) Field of Classification Search
USPC ...................................... 606/62–68
See application file for complete search history.

(56) References Cited

U.S. PATENT DOCUMENTS

| | | | |
|---|---|---|---|
| 4,475,545 A | 10/1984 | Ender | |
| 4,622,959 A | 11/1986 | Marcus | |
| 5,549,610 A * | 8/1996 | Russell et al. | 606/64 |
| 6,106,528 A * | 8/2000 | Durham et al. | 606/64 |
| 6,221,074 B1 | 4/2001 | Cole et al. | |
| 6,322,562 B1 * | 11/2001 | Wolter | 606/62 |
| 7,247,157 B2 | 7/2007 | Prager et al. | |
| 7,670,340 B2 * | 3/2010 | Brivio et al. | 606/64 |
| 7,726,002 B2 | 6/2010 | Shimp et al. | |
| 7,914,532 B2 | 3/2011 | Shaver et al. | |
| 2001/0034524 A1 * | 10/2001 | Bales | 606/73 |
| 2004/0138662 A1 * | 7/2004 | Landry et al. | 606/61 |
| 2005/0055023 A1 * | 3/2005 | Sohngen et al. | 606/62 |
| 2006/0064095 A1 | 3/2006 | Senn et al. | |
| 2006/0095040 A1 | 5/2006 | Schlienger et al. | |
| 2006/0229607 A1 * | 10/2006 | Brumfield | 606/61 |
| 2007/0208373 A1 * | 9/2007 | Zaver et al. | 606/200 |
| 2008/0287949 A1 * | 11/2008 | Keith et al. | 606/62 |
| 2011/0282395 A1 * | 11/2011 | Beyar et al. | 606/301 |

FOREIGN PATENT DOCUMENTS

| | | |
|---|---|---|
| EP | 1440664 A2 | 7/2004 |
| WO | 2011002903 A2 | 1/2011 |

OTHER PUBLICATIONS http://environmentalchemistry.com/yogi/periodic/Au.html, accessed Oct. 16, 2013.*

* cited by examiner

*Primary Examiner* — Jan Christopher Merene
(74) *Attorney, Agent, or Firm* — Lerner, David, Littenberg, Krumholz & Mentlik, LLP

(57) ABSTRACT

A system is proposed including an intramedullary nail with a longitudinal nail axis, a first lateral portion, a second lateral portion opposite to the first lateral portion, and a longitudinal bore. The nail has a locking hole arrangement having a first bore being formed in the first lateral portion and a second bore being formed in the second lateral portion. An axis of the first bore and an axis of the second bore are arranged with an offset from each other, and are arranged so that a locking member such as a screw may frictionally engage within both the first bore and the second bore.

29 Claims, 3 Drawing Sheets

INTRAMEDULLARY NAIL LOCKING HOLE ARRANGEMENT

BACKGROUND OF THE INVENTION

The invention generally relates to an intramedullary nail. Particularly, the invention relates to an intramedullary nail and a locking member, wherein the intramedullary nail comprises a locking hole arrangement for angularly stable receipt of the locking member. The locking member may be, for example, a cross-locking bone screw. A method of implanting such a nail is also disclosed.

In general, an intramedullary nail may be for example a femur nail, a humeral nail or a tibia nail. Usually, the leading end portion which may at first be introduced into a medullary channel of a bone and which may also be denoted as non-driving end portion of the intramedullary nail, comprises two or more through holes adapted to receive locking screws.

At present inserting locking screws in holes formed in the leading end of implanted intramedullary nails is problematic, namely because of the amount of radiation required during the determination of the position and orientation of transverse locking holes. Furthermore, it is time consuming and ideally requires well-trained and experienced personal. Therefore, it has a significant influence of the overall operation room time required.

Currently, locking of the non-driving end portion of an intramedullary nail is performed mostly freehand, by inserting a first locking screw into and through a first through hole. Due to the fact that the insertion is performed more or less blindly, the screw will in most cases not exactly hit the through hole so that the nail will be slightly displaced or even deformed to accommodate the locking screw extending through the through hole. However, this first screw will be able to move relative to the nail when forces are applied on the nail and screw.

For a locking providing angular stability, a second screw may be inserted through a second through hole adjacent the first hole. Also the second screw will in most cases not exactly hit the second through hole. Accordingly, the second screw has to be urged through the hole, with the result that the combination of the first and second screws will provide an angle-stable fixation of the intramedullary nail, i.e. a fixation with no movement of a screw relative to the nail.

However, such a fixation of an intramedullary nail requires the insertion of two screws, wherein each insertion of a screw through the leading end portion of an intramedullary nail is difficult and thus time consuming.

According to U.S. Pat. No. 7,247,157, a deformable ring may be arranged between a threaded bore and the thread of a bone screw to achieve an angle-stable locking. U.S. Patent Application Publication No. 2006/0095040 proposes a deformable sleeve on a locking screw, for introducing the screw backlash-free into a transverse hole of a marrow nail. Alternatively, U.S. Patent Application Publication No. 2006/0064095 proposes a passage extending through a screw head and an external thread generally parallel the longitudinal axis of the screw for accommodating a longitudinal wedge element. As a result, any gap between the locking screw and an intramedullary nail is eliminated and the screw is wedged in position in a transverse hole of the intramedullary nail.

BRIEF SUMMARY OF THE INVENTION

It may be seen as a need to make locking of the non-driving end portion of intramedullary nails easier. In general, it is of interest to shorten the operation room time which is beneficial not only for the patient under anaesthesia, but ultimately reduces costs.

This is achieved by the subject-matter of each of the independent claims. Further embodiments are described in the respective dependent claims.

In general, an intramedullary nail according to the invention comprises a longitudinal nail axis, a first lateral portion, a second lateral portion opposite to the first lateral portion, a longitudinal bore, and a locking hole arrangement having a first bore with a first bore axis, wherein the first bore is formed in the first lateral portion and communicates with the longitudinal bore, and a second bore with a second bore axis, wherein the second bore is formed in the second lateral portion and communicates with the longitudinal bore. The first bore axis and the second bore axis are arranged with an offset between each other, and are arranged so that a locking member is insertable through both the first bore and the second bore.

An intramedullary nail with a longitudinal bore, i.e. with a through bore extending along a longitudinal axis of the intramedullary nail, may also be denoted as cannulated intramedullary nail, or as a hollow nail.

A lateral portion of a hollow or cannulated intramedullary nail may be understood as a portion forming substantially half of the circumference of the nail and extending in a longitudinal direction of the nail. In other words, a first and a second lateral portion may be achieved by cutting an intramedullary nail along its longitudinal axis.

According to an embodiment of the invention, the first bore comprises a first bore diameter and the second bore comprises a second bore diameter, wherein the offset is smaller than 20 percent of the first bore diameter and is smaller than 20 percent of the second bore diameter, wherein the first bore diameter may be equal to the second bore diameter.

According to another embodiment of the invention, the first bore axis is arranged parallel to the second bore axis. It will be understood that the two axes may also be orientated inclined relative to each other, wherein the axes may or may not intersect each other.

According to an embodiment of the invention, the first bore axis and the second bore axis are arranged with an offset in a direction of the nail axis. According to a further embodiment of the invention, the first bore axis and the second bore axis are arranged with an offset perpendicular to the nail axis. It will be understood that the intended angle-stable fixation may also be achieved with two bores the bore axes of which are arranged with an offset in any direction other than the direction of the nail axis or the direction perpendicular to the nail axis, i.e. inclined to these directions. In other words, the offset may have a component both in the direction of the nail axis and in the direction perpendicular to the nail axis.

According to a further embodiment of the invention, the first bore axis and the second bore axis intersect the nail axis.

According to another embodiment of the invention, the first bore axis and the second bore axis are arranged perpendicular to a plane including the nail axis. This means that a bore axis may pass the nail axis without intersecting the same.

For example, the first bore axis may pass the nail axis with a distance of 0.3 mm on a first side of the axis, and the second bore axis may pass the nail axis with a distance of 0.3 mm on a second side, i.e. opposite side, of the nail axis.

According to an embodiment of the invention, the first bore diameter is smaller than 60 percent of a nail diameter and the second bore diameter is also smaller than 60 percent of the nail diameter.

A longitudinal bore diameter may be smaller than 60 percent of a nail diameter. Furthermore, a longitudinal bore axis may be coaxial or congruent with the longitudinal nail axis.

For example, the nail diameter may be 10 mm, the diameter of the first and second bores may be 5.1 mm, and the diameter of the longitudinal bore may be 5 mm. For accommodating a 5 mm universal screw, an appropriate offset may be 0.6 mm in this example.

According to a further embodiment of the invention, a system includes an intramedullary nail and a first locking member having a first locking member diameter, wherein the first locking member diameter is smaller than the first bore diameter and greater than the first bore diameter minus the offset, and is smaller than the second bore diameter and greater than the second bore diameter minus the offset.

It is noted that, although a screw may be a preferred locking member, also a bolt or nail may be use as locking member, since also a locking member without threads may frictionally engage within the first and second bores. A nail or bolt may have, instead of threads, a smooth outer surface or alternatively a rough surface, wherein a rough surface may be a surface formed with any kind of notches or impressions.

In case the locking member is a screw, it will be understood that a first screw thread of the first locking member may be formed so that the first screw thread can frictionally engage within the first and second bores, due to the offset between these bores.

The term 'frictionally engage' should be understood as firmly fixed in a transverse direction, i.e. not enabling any movement of the locking member transverse to its axis relative to the nail, but allowing the locking member to be moved in a longitudinal direction of the locking member, for example by screwing the locking member in or out of the hole arrangement.

When for example a screw is screwed in a hole arrangement, the screw thread may cause a deformation of an edge of at least one of the bores, or the screw thread may cut into a surface of at least one of the bores, so that a well defined connection between the screw and the nail is formed. In this case, the material of the screw is harder than the material of the nail.

According to yet another embodiment of the invention, the material of the nail is harder than the material of the locking member so that the locking member or at least a part of the outer surface of the locking member will be deformed when the locking member is introduced through the locking hole arrangement, wherein said outer surface may be defined by threads of a screw.

According to yet a further embodiment of the invention, a system with the intramedullary nail may further comprise a second locking member having a second locking member diameter, wherein the second locking member diameter is smaller than the first bore diameter minus the offset and smaller than the second bore diameter minus the offset.

It should be pointed out that the locking member or screw denoted as first locking member or first screw is adapted for an angle-stable fixation of the nail, and that the locking member or screw denoted as second locking member or second screw is adapted for a non-angle-stable fixation of the nail.

Furthermore, it is noted that a system according to the invention may comprise an intramedullary nail including at least one locking hole arrangement, together with at least one first locking member or first screw and/or at least one second locking member or second screw, for example depending on the preferences of a physician utilizing the system.

A method according to the invention comprises the steps of implanting an intramedullary nail as described above, inserting a locking member through the locking hole arrangement in the intramedullary nail, and deforming at least one of the locking member and the walls of the locking hole arrangement, due to an offset of two bores of the locking hole arrangement and thus a frictional engagement of the locking member with the locking hole arrangement.

The aspects defined above and further aspects, features and advantages of the present invention can also be derived from the examples of the embodiments to be described hereinafter and are explained with reference to examples of the embodiments to which the invention is not limited.

Aspects are achieved by an intramedullary nail having an elongated shaft with a longitudinal bore extending along a longitudinal axis of the shaft. The shaft has first and second longitudinal portions formed by a plane along the longitudinal axis, each portion partially surrounding the longitudinal bore. A first bore having a first diameter extends through the first longitudinal portion along a first axis transverse to the longitudinal axis and a second bore is spaced from the first bore by the longitudinal bore, the second bore having a second diameter and extends through the second longitudinal portion along a second axis transverse to the longitudinal axis. The first and second axis are offset such that the spaced first and second bore diameters overlap with respect to the longitudinal axis. The first and second bore axes may be parallel and the first and second bore diameters may be equal. The first and second bore axis may be offset by less than 20% of the bore diameter. The first bore axis and second bore axis may be offset in the direction of the shaft longitudinal axis. The first bore axis and second bore axis may be offset in a direction perpendicular to the longitudinal shaft axes.

A method for implanting an intramedullary nail comprises implanting the intramedullary nail in a bone canal. The nail has a longitudinal nail axis, a first lateral portion, a second lateral portion opposite the first lateral portion, a longitudinal bore, a first bore with a first bore axis wherein the first bore is formed in the first lateral portion and communicates with the longitudinal bore. A second bore with a second bore axis is formed in the second lateral portion of the rod and communicates with the longitudinal bore. The first bore axis and the second bore axis are arranged with an offset between each other, and are arranged so that a single locking member is insertable through both the first bore and the second bore in a bone canal. The locking member is inserted through the first and second bores at a non-zero angle to the first and second axis and frictionally engages portions of the first and second bore. The locking member may be a bone screw.

BRIEF DESCRIPTION OF THE DRAWINGS

The invention will now be detailed by way of an exemplary embodiment with reference to the attached drawings.

It is noted that the illustration in the drawings is only schematically and not to scale. In different figures, similar elements are provided with the same reference signs.

DETAILED DESCRIPTION

Figure 1:
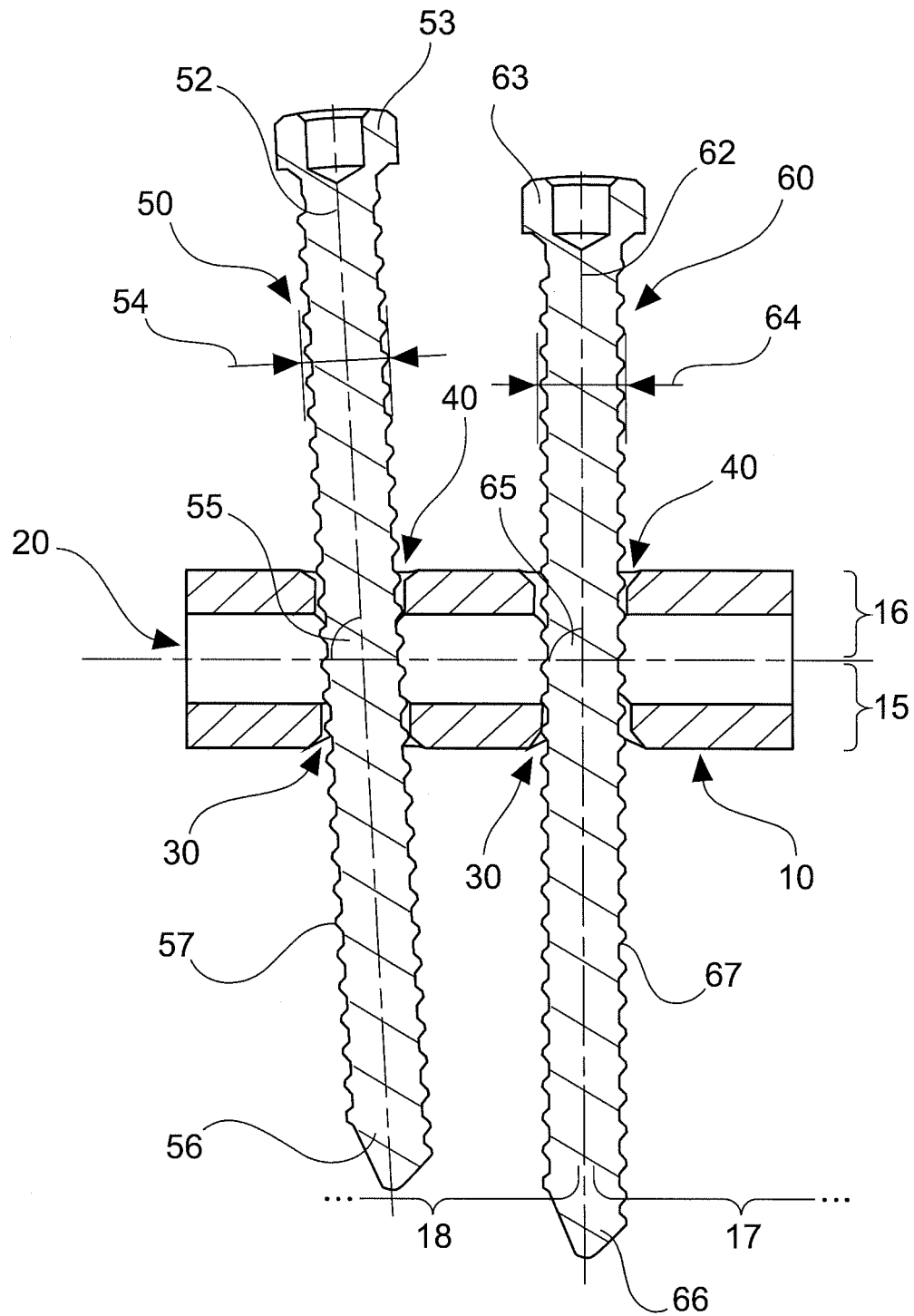
FIG. 1 illustrates a section view of an intramedullary nail together with a first screw for angle-stable locking of the nail and a second screw for non-angle-stable locking of the nail, according to the invention.

FIG. 1 is an illustration showing a section of an intramedullary nail 10 with a longitudinal bore 20. The nail comprises a first lateral portion 15, i.e. substantially the lower half of the nail, and a second lateral portion 16, i.e. substantially the upper half of the nail (as depicted in FIG. 1). Further, the nail 10 comprises two hole arrangements each including a first bore 30 formed in the first lateral portion 15, and a second bore 40 formed in the second lateral portion 16.

In FIG. 1, a first screw 50 is inserted into the left hole arrangement. The first screw 50 includes a first screw head 53, a first screw tip 56 and a first screw thread 57. Further, the first screw 50 comprises a first screw axis 52 and a first screw diameter 54. It will be understood that the screw diameter is an overall outer diameter of the screw. While the screw diameter is less than the bore diameters it may be large enough to slidably engage sides of the bores.

The first screw 50 is adapted for an angle-stable fixation of the nail 10. Accordingly, the first screw diameter 54, the form and dimension of the first screw thread 57, as well as the diameters of the first and second bores 30, 40, and the offset between these bores are closely interrelated or interdependent to each other. Therefore, the first screw 50 is arranged with an angle 55 relative to the longitudinal axis of the nail 10, wherein the angle 55 may be orthogonal to the nail axis, but will in most cases not be orthogonal to the nail axis.

Also in FIG. 1, a second screw 60 is shown, inserted into the right hole arrangement. The second screw 60 includes a second screw head 63, a second screw tip 66 and a second screw thread 67. Further, the second screw 60 comprises a second screw axis 62 and a second screw diameter 64.

The second screw 60 is adapted for a non-angle-stable fixation of the nail 10. Accordingly, the second screw diameter 64, as well as the diameters of the first and second bore 30, 40, together with the offset between these bores are also but not in the same way as the first screw closely interrelated and interdependent to each other. Therefore, the second screw 60 is arranged with an angle 65 relative to the longitudinal axis of the nail 10, which angle 65 may be, in many cases, orthogonal to the nail axis.

To achieve on the one hand an angle-stable fixation and on the other hand a non-angle-stable fixation, the first screw diameter 54 may be greater than the second screw diameter 64. As can be seen in FIG. 1, the first bore 30 and the second bore 40 of the left hole arrangement are substantially occupied by the first screw 50, whereas the first bore 30 and the second bore 40 of the right hole arrangement are not completely filled by the second bore 60, but leave a small area free, i.e. on the right side in the first bore 30 and on the left side in the second bore 40.

Figure 2:
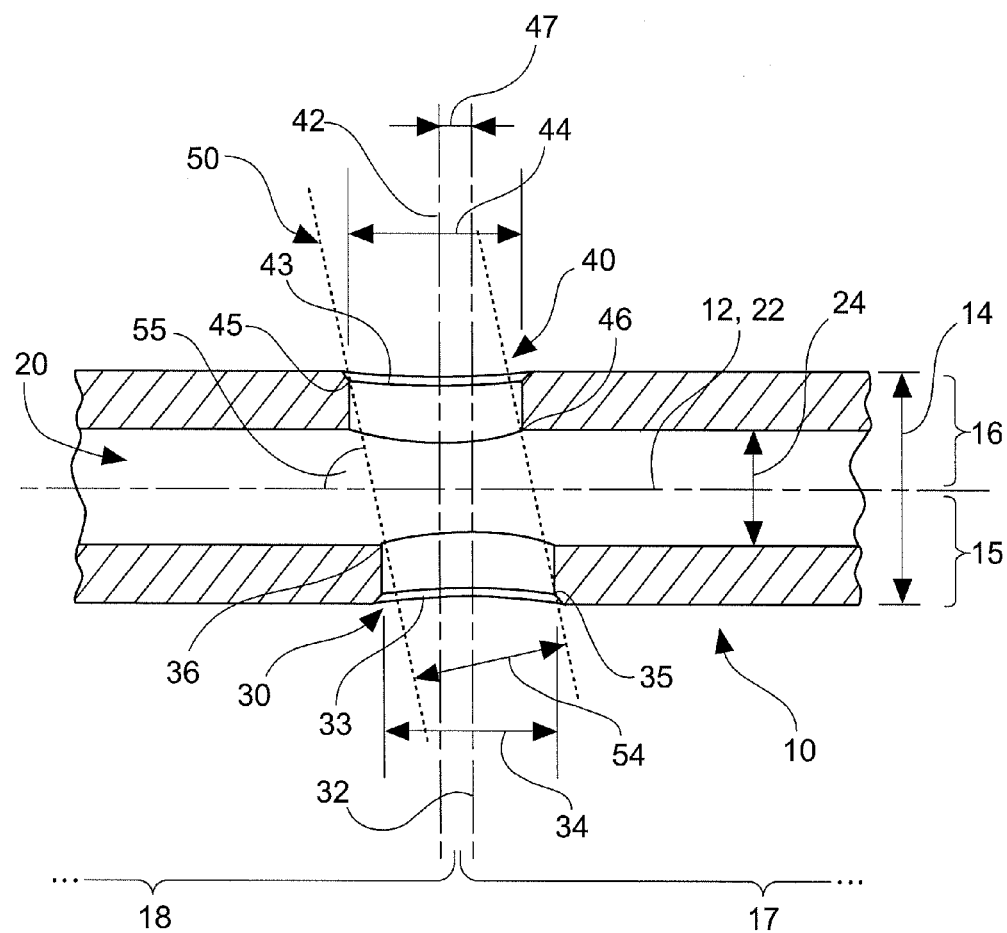
FIG. 2 is a schematical illustration of a locking hole arrangement of an intramedullary nail according to the invention.

FIG. 2 is an illustration of the cannulated intramedullary nail 10 having a longitudinal bore 20, a first bore 30 in a first lateral portion 15 and a second bore 40 in a second lateral portion 16.

The nail 10 includes a longitudinal nail axis 12 and a nail diameter 14. The longitudinal bore 20 is defined by the longitudinal bore axis 22 and the longitudinal bore diameter 24. In this exemplary embodiment, the longitudinal nail axis 12 is coaxial or congruent to the longitudinal bore axis 22.

The first bore 30 has a first bore axis 32 and a first bore diameter 34. Correspondingly, the second bore 40 comprises a second bore axis 42 and a second bore diameter 44. Furthermore, a first bore chamfer 33 is formed as a transition from the surface of the first bore 30 to the outer surface of the nail 10, i.e. to the outer surface of the first lateral portion 15 of the nail 10, and a second bore chamfer 43 is formed as a transition from the surface or the second bore 40 to the outer surface of the nail 10, i.e. to the outer surface of the second lateral portion 16 of the nail.

Further illustrated in FIG. 2 is an offset 47 between the first bore axis 32 and the second bore axis 42. In this exemplary embodiment, the offset 47 is arranged substantially in a direction of the longitudinal axis 12 of the nail 10.

In dashed lines, a first locking member 50 which may be a bolt, nail or a screw, is illustrated extending through both the first bore 30 and the second bore 40. The first locking member diameter 54 is smaller than the first and second bore diameters 32, 42, but due to the offset 47, the outer edges of the first locking member engage a first contact point 35, a second contact point 36, a third contact point 45 and a fourth contact point 46. It will be understood that each contact point includes an area defined by a section of an edge together with a section of the wall surface adjacent this edge of a respective bore.

In the exemplary embodiment of FIG. 2, the first contact point 35 is at an outer edge of the first bore, at the first lateral portion 15 and at a first longitudinal portion 17 of the nail 10. The second contact point 36 is at an inner edge of the first bore 30, at the first lateral portion 15 and at a second longitudinal portion 18 of the nail 10. The third contact point 45 is at the outer edge of the second bore 40, at the second lateral portion 16 and at the second longitudinal portion 18 of the nail. The fourth contact point 46 is at an inner edge of the second bore 40, at the second lateral portion 16 and at the first longitudinal portion 17 of the nail. Thus, the first screw 50 is positioned with an inclined angle 55 relative to the longitudinal nail axis 12.

The first locking member/screw, the left one in FIG. 1, may deform the outer edge of the first bore at the first contact point, may deform the inner edge of the first bore at the second contact point, may cut into the side wall of the second bore at the third contact point, and may deform and cut the inner edge of the second bore at the fourth contact point.

Figure 3:
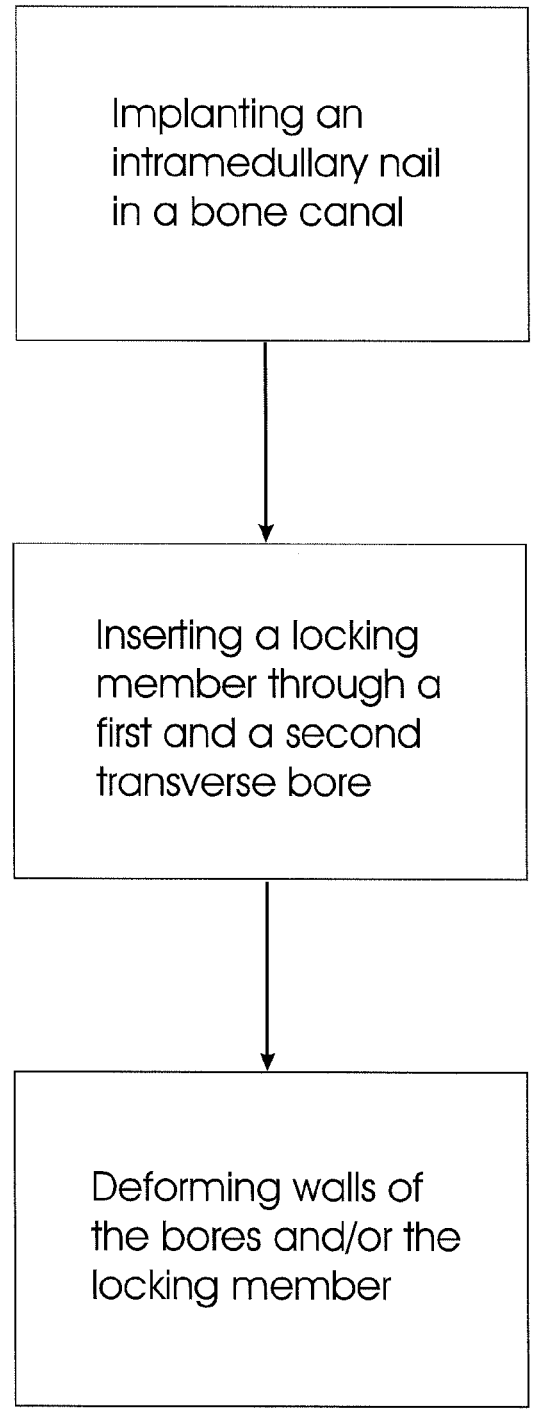
FIG. 3 is a flow-chart including major steps of a method according to the invention.

The flow-chart in FIG. 3 illustrates the principle of the steps performed in accordance with the invention. It will be understood that the steps described, are major steps, wherein these major steps might be differentiated or divided into several sub-steps. Furthermore, there might be also sub-steps between these major steps. Therefore, a sub-step is only mentioned if this step may be important for the understanding of the principles of the method according to the invention.

In a first step, and intramedullary nail according to the invention may be implanted into a bone canal. It is noted, that an intramedullary nail is usually implanted to fix at least two fractured bone fragments relative to each other. Accordingly, locking screws are used at both ends of the intramedullary nail, each fixing a bone fragment relative to the nail.

In a next step, a locking member, like a locking screw, is inserted in a transverse direction to the nail through a first bone portion and into a first bore formed in the nail. By further driving in of the locking member, the tip of the locking member will also be inserted into a second bore formed with an offset and opposite to the first bore. Due to the offset, a force will act between the locking member and the walls of the bores.

The force acting between the locking member and the walls of the bores subsequently deforms at least one of the locking member and the walls of the bores, depending on the respective hardness of these elements. For example, when the locking member is made from a material which is harder than the material of the nail, substantially the walls of the bores will be deformed. On the other hand, when the nail is made from a material which is harder than the material of the locking member, substantially the outer surfaces of the locking member, for example the threads of a locking screw, will be deformed, wherein also a bending of the shaft of the locking member may occur. It will be understood, that the locking member as well as the walls of the bores will be deformed, when the respective materials comprise a similar hardness.

By way of this deformation, an accurate fitting engagement between the locking member and the nail will be achieved, being a force fit engagement.

While the invention has been illustrated and described in detail in the drawings and foregoing description, such illustration and description are to be considered illustrative or exemplary and not restrictive. The invention is not limited to the disclosed embodiments.

Other variations to the disclosed embodiments can be understood and effected by those skilled in the art in practising the claimed invention, from the study of the drawings, the disclosure and the appended claims. In the claims, the word "comprising" does not exclude other elements and indefinite article "a" or "an" does not exclude a plurality. The mere fact that certain measures are recited in mutual different dependent claims does not indicate that a combination of these measures cannot be used to advantage. Any reference signs in the claims should not be construed as limiting the scope.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An intramedullary nail, the nail comprising:
   a longitudinal nail axis,
   a first lateral portion,
   a second lateral portion opposite to the first lateral portion,
   a longitudinal bore,
   a first cylindrical bore extending only partially through the nail from the first lateral portion towards the second lateral portion wherein the first cylindrical bore has a first diameter and a first longitudinal central axis formed in the first lateral portion and intersects with the longitudinal bore defining a first inner edge portion along the intersection of the first bore and the longitudinal bore,
   a second cylindrical bore extending only partially through the nail from the second lateral portion towards the first lateral portion wherein the second bore has a second diameter and a second longitudinal central axis formed in the second lateral portion and intersects with the longitudinal bore defining a second inner edge portion along the intersection of the second bore and the longitudinal bore, and
   wherein the first bore longitudinal central axis and the second bore longitudinal central axis are parallel and are spaced along the longitudinal nail axis such that the first and second cylindrical bores overlap to produce a bore overlap that is not a circle, the overlap located between the first to the second lateral portions;
   a threaded, locking screw having a diameter greater than a minimum dimension of the overlap opening, the screw insertable through both the first bore and the second bore and the screw thread of the locking screw capable of deforming at least one of the first and second inner edge portions.

2. The intramedullary nail according to claim 1, wherein the first cylindrical bore comprises a first bore diameter and the second bore comprises a second cylindrical bore diameter, wherein the offset is smaller than 20 percent of the first bore diameter and is smaller than 20 percent of the second bore diameter.

3. The intramedullary nail according to claim 2, wherein the first bore diameter is equal to the second bore diameter.

4. The intramedullary nail according to claim 1, wherein the first bore longitudinal central axis is arranged parallel to the second bore longitudinal central axis.

5. The intramedullary nail according to claim 1, wherein the first bore longitudinal central axis and the second bore longitudinal central axis are arranged with an offset in a direction of the nail axis.

6. The intramedullary nail according to claim 1, wherein the first bore longitudinal central axis and the second bore longitudinal central axis are arranged with an offset along the nail axis.

7. The intramedullary nail according to claim 1, wherein the first bore longitudinal central axis and the second bore longitudinal central axis are arranged perpendicular to a plane including the nail axis.

8. The intramedullary nail according to claim 1, wherein at least one of the first bore longitudinal central axis and the second bore longitudinal central axis intersect the longitudinal nail axis.

9. The intramedullary nail according to claim 1, wherein a first bore diameter is smaller than 60 percent of a nail diameter, and wherein a second bore diameter is smaller than 60 percent of the nail diameter.

10. The intramedullary nail according to any claim 1, wherein a longitudinal bore diameter is smaller than 60 percent of a nail diameter.

11. The intramedullary nail according to claim 1, wherein a longitudinal bore central axis is coaxial with the longitudinal nail axis.

12. A system comprising:
    an intramedullary nail according to claim 1, and
    a first locking screw having a first diameter, wherein the first locking screw diameter is smaller than the first bore diameter and greater than a first bore diameter minus the offset, and is smaller than a second bore diameter and greater than the second bore diameter minus the offset.

13. The system according to claim 12, wherein the locking screw includes a first screw thread which is formed so that the first screw thread can frictionally engage with both the first bore and the second bore.

14. The system according to claim 12, wherein the first locking screw has a first locking screw material and the nail has a nail material, wherein the first locking screw material is harder than the nail material.

15. The system according to claim 12, wherein the first locking screw has a first locking screw material and the nail has a nail material, wherein the nail material is harder than the first locking screw material.

16. The system according to claim 12, further comprising a second locking screw having a second diameter, wherein the second locking screw diameter is smaller than the first bore diameter minus the offset and smaller than the second bore diameter minus the offset.

17. A system comprising:
    an intramedullary nail according to claim 1 further comprising
    a second locking screw having a second locking screw diameter, wherein the second locking screw diameter is smaller than a first bore diameter minus the offset and smaller than a second bore diameter minus the offset.

18. An intramedullary nail comprising:
    an elongated shaft with a longitudinal bore extending along a central longitudinal axis of the shaft, the shaft having first and second longitudinal portions formed by a plane along the central longitudinal axis, each portion partially surrounding the longitudinal bore, a first circular bore having a first diameter extends through the first longitudinal portion and intersects the longitudinal bore along a first bore longitudinal central axis transverse to the central longitudinal axis of the shaft and a second circular bore spaced from the first bore by the longitudinal bore, the second bore having a second diameter and extends through the second longitudinal portion and intersects the longitudinal bore along a second bore longitudinal central axis transverse to the longitudinal shaft axis, the first and second bore forming first and second circumferential edges at the intersection of the longitudinal bore, the first and second bore longitudinal central axes offset along the longitudinal shaft central axis such that the spaced first and second bore diameters overlap a distance with respect to the longitudinal shaft axis; and a locking screw having a diameter greater than the overlap distance of the first and second bores such that an interference between the screw and portions of at least one of the first and second circumferential edges causes a deformation of a portion of the at least one first and second edges.

19. The intramedullary nail as set forth in claim 18 wherein the first and second bore longitudinal central axes are parallel.

20. The intramedullary nail as set forth in claim 19 wherein the first and second bore diameters are equal.

21. The intramedullary nail as set forth in claim 20 wherein the first and second bore longitudinal central axes are offset by less than 20% of the bore diameter.

22. The intramedullary nail as set forth in claim 18 wherein the first bore longitudinal central axis and second bore longitudinal central axis are offset in the direction of the shaft longitudinal axis.

23. The intramedullary nail as set forth in claim 18 wherein the first bore longitudinal central axis and second bore longitudinal central axis are offset in a direction perpendicular to the first and second bore longitudinal central axes.

24. A method for implanting an intramedullary nail comprising:

implanting an intramedullary nail in a bone canal, the nail comprising:

a longitudinal nail axis;

a first lateral portion;

a second lateral portion extending along the longitudinal nail axis opposite to the first lateral portion;

a longitudinal bore extending along the longitudinal nail axis;

a first circular bore with a first bore longitudinal central axis wherein the first bore is formed in the first lateral portion and intersects with the longitudinal bore and forms a first arcuate edge portion along the intersection of the first bore and the longitudinal bore;

a second circular bore with a second bore longitudinal central axis, wherein the second bore is formed in the second lateral portion and intersects with the longitudinal bore and forms a second arcuate edge portion along the intersection of the second bore and the longitudinal bore;

wherein the first bore longitudinal central axis and the second bore longitudinal central axis extend transverse to the longitudinal nail axis and are arranged with an offset between each other, and are arranged so that a single locking member is insertable through both the first bore and the second bore;

inserting a bone screw through the first and second bores at a non-zero angle to the first and second bore longitudinal central axes; and deforming a portion of at least one of the first and second arcuate edge portions of the first and second bore with the locking member, the deformed portion lying in a plane containing the longitudinal nail axis and the first and second central axis.

25. The method as set forth in claim 24 wherein the locking member is a bone screw.

26. The method as set forth in claim 25 wherein the first and second longitudinal central axes are perpendicular to the longitudinal nail axis.

27. The method as set forth in claim 26 wherein the first and second circular bores are offset along the longitudinal nail axis.

28. An intramedullary nail comprising:

a bone nail having a first and second end;

a longitudinal nail axis;

a first lateral portion;

a second lateral portion opposite to the first lateral portion;

a longitudinal bore;

a first circular bore having a first bore longitudinal central axis, wherein the first bore is formed in the first lateral portion defining a first outer edge portion and intersects with the longitudinal bore defining a first inner edge portion along the intersection of the first bore and the longitudinal bore;

a second circular bore having a second bore longitudinal central axis, wherein the second bore is formed in the second lateral portion defining a second outer edge portion and intersects with the longitudinal bore defining a second inner edge portion along the intersection of the second bore and the longitudinal bore; and a locking screw for insertion through the first and second circular bores, wherein the first bore longitudinal central axis and the second bore longitudinal central axis are parallel and arranged with an offset between each other with respect to the longitudinal axis, the locking screw having an outer diameter sized such that the offset causes the outer diameter of the locking screw to contact and deform at least one of the first and second inner or outer circumferential edge portions upon insertion through the first and second bores.

29. The intramedullary nail as set forth in claim 28 wherein the locking screw contacts and deforms one of the first and second inner and outer circumferential edge portions closest to the nail first end and one of the first and second inner and outer circumferential edge portions closest to the nail second end.

* * * * *